US 8,448,077 B2

(12) United States Patent
Alsafadi

(10) Patent No.: US 8,448,077 B2
(45) Date of Patent: May 21, 2013

(54) DECISION SUPPORT SYSTEMS FOR GUIDELINE AND KNOWLEDGE NAVIGATION OVER DIFFERENT LEVELS OF ABSTRACTION OF THE GUIDELINES

(75) Inventor: Yasser H. Alsafadi, Yorktown Heights, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 754 days.

(21) Appl. No.: 11/576,367

(22) PCT Filed: Sep. 22, 2005

(86) PCT No.: PCT/IB2005/053132
§ 371 (c)(1),
(2), (4) Date: Mar. 30, 2007

(87) PCT Pub. No.: WO2006/035383
PCT Pub. Date: Apr. 6, 2006

(65) Prior Publication Data
US 2008/0097965 A1    Apr. 24, 2008

Related U.S. Application Data

(60) Provisional application No. 60/614,715, filed on Sep. 30, 2004.

(51) Int. Cl.
*G06F 17/30* (2006.01)
(52) U.S. Cl.
USPC .......................... 715/764; 715/971; 715/702
(58) Field of Classification Search
USPC .............. 715/702, 764, 971; 707/3, E17.014
See application file for complete search history.

(56) References Cited

U.S. PATENT DOCUMENTS 7,230,529 B2 * 6/2007 Ketcherside et al. .... 340/539.12
2004/0172294 A1 * 9/2004 Dahlin et al. ...................... 705/2
2004/0260576 A1 * 12/2004 Wang et al. ........................ 705/2

OTHER PUBLICATIONS

"A Guideline Management System", Ciccarese, P. et al. Medinfo. 2004, vol. 11, Sep. 2004.
"Patient Workflow Management System built on Guidelines", Dazzi, L. et al., Conference of the American Medical Infomatics Association, 1997.
"Guideline-based Careflow Systems", Quaglini, S. et al., Artifical Intelligence in Medicine, Aug. 2000.
"The Urgent Need to Improve Health Care Quality", by Chassin, M. et al., JAMA, vol. 280, No. 11, Sep. 1998.
"Persons with Chronic Conditions. Their Prevalence and Costs", Hoffman, C. et al. Abstract Only.
Greenes, R. A., Ed.; Clinical Decision Support-The Road Ahead; 2007; Elsevier, Inc., Oxford, UK; pp. 31-45, 367-269, 281-303.

* cited by examiner

*Primary Examiner* — Chat C. Do
*Assistant Examiner* — Andrea Leggett

(57) ABSTRACT

A system and method are provided for executing an executable clinical practice guideline for providing guidance in treating a patient. A guideline repository stores a plurality of executable clinical practice guidelines. At least one interface receives clinical context data associated with at least one of the patient and the patient's treatment. A system server, upon receipt of said clinical context data, automatically chooses an appropriate guideline and controls a display to display the guideline at its present level of abstraction, and a visual navigator which defines the current level of abstraction. The level of abstraction is changed via a user input between a higher level of abstraction in which fewer more abstract steps of the guidelines are displayed and a lower level of abstraction in which more, detailed steps are displayed.

20 Claims, 3 Drawing Sheets

DECISION SUPPORT SYSTEMS FOR GUIDELINE AND KNOWLEDGE NAVIGATION OVER DIFFERENT LEVELS OF ABSTRACTION OF THE GUIDELINES

The present invention relates to clinical decision support systems (DSSs), and more particularly to the use of DSSs for navigating technical practice guidelines, e.g., clinical healthcare practice and treatment guidelines (CDSSs), over differing levels of abstraction in accord with the context of practice (care), where the correct guideline and the level of detail are automatically defined by context, or manually controllable by a user of the DSS.

Available evidence shows that the American health care delivery system requires significant adjustments to close the gap between delivered healthcare and needed healthcare. Statistics show that scientific knowledge available today could be more readily relied upon to influence the quality of health care ultimately received, that as medical science and technology have advanced at a rapid pace in recent years, the American healthcare system frequently falls short in its ability to translate knowledge into practice, and apply new technology safely and appropriately. Statistics show further that the performance of the American healthcare system, i.e., quality of care, varies considerably, and can be substantially readily improved if based upon evidence rather than incumbent treatment practices.

The Committee on the Quality of Healthcare in America was formed in June 1998, and charged with developing a strategy in view of the current state of US healthcare which would result in substantial improvement in the quality of healthcare over the next ten (10) years. INSTITUTE OF MEDICINE, CROSSING THE QUALITY CHASM, National Academy Press, Wash., DC; 2002 (hereinafter referred to as "the IOM Report" or "the Committee Report"). "Research on the quality of care reveals a health care system that frequently falls short in its ability to translate knowledge into practice and apply new technology safely and appropriately"; IOM report at pages 2-3. The performance of the American health-care system varies considerably. "A highly fragmented delivery system that largely lacks rudimentary clinical information capabilities results in poorly designed care practices characterized by unnecessary duplication of services and long waiting times and delays." IOM Report at page 3. And there is substantial evidence documenting overuse of many services. Chassin, et al., The Urgent Need To Improve Health Care Quality, JAMA 280(11): 100-5 1998; Shuster, et al., How Good Is The Quality Of Health Care In The United States?, The Millbank Quarterly, 76(4):517-63 1998.

The IOM Committee further observed that in the last several decades, the needs of the American public have been shifting from predominantly acute, episodic care, to care for chronic conditions, accounting for a majority of health care expenditures. Hoffman, et al., Persons With Chronic Conditions, Their Prevalence and Costs, JAMA 276 (18): 1473-79 (1996); The Robert Wood Johnson Foundation, Chronic Care In America: A 21$^{st}$ Century Challenge, Princeton, N.J.: The Robert Wood Johnson Foundation, 1996. In their efforts to find a solution to what they interpret as an American health care crisis, the IOM Committee has provided a suggested agenda as a road map for implementing changes in practice guidelines which should have a synergistic effect in improving delivered health care in this country, and of course, worldwide.

The IOM Committee agenda is based upon six (6) aims: safety, effectiveness, patient-centeredness, timeliness, efficiency and equity, and suggest various innovations to achieve the goals in a set of rules to guide the redesign of the American Health Care System. The IOM Committee characterizes their agenda as "carefully and consciously designed to provide health care that is safe, client-centered, timely, efficient and equitable," to serve the needs of the patient and to ensure that each patient is fully informed, retain control and participate in care delivery whenever possible, and receive care that is respectful of these values and preferences. The IOM report strongly recommends the implementation of a rules-based system, the operation of which requires the application of scientific knowledge to practice, and provide clinicians with the tools and support necessary to deliver evidence-based care consistently and safely, i.e., evidence-based care. The IOM Report, pgs. 5-9.

Evidence-based care and decision making is supported by the principle that patients should receive care based on the best available scientific knowledge. Evidence-based practice is the integration of best research evidence with clinical expertise and patient values. The intended result of evidence-based decision-making in the practice of medicine is that its implementation will see that care is not illogically varied from physician to physician (practice to practice).

The Committee understands that implementing a change to the present state of health care in the US, in moving towards a future goal that all health care be evidence-based, is an enormous undertaking, and must be accomplished in steps over time. So they suggest a stepwise approach to implementation, by first establishing care processes which focus attention on maladies affecting many people. About 15 to 25 maladies account for the majority of health care services provided by the US health care system. Centers For Disease Control and Prevention (1999), nearly all of which are chronic.

Care for chronically ill needs to be a collaborative, multidisciplinary process. Effective methods of communicating personal health information are essential. Carefully designed evidence-based care processes, supported by annotated clinical information and decision support systems are highly recommended in the IOM Report. But while efforts are now under way to synthesize clinical evidence pertaining to common chronic conditions, the only way to realize value from a guideline or knowledge database is by making it available. It is a given based on the existing evidence that improvement of the effectiveness of patient care is achievable using computer-based implementation of executable clinical practice guidelines integrated with clinical workflow, e.g., an ability to provide patient specific recommendations at points of care. Executable guidelines make knowledge readily available to the clinician, without the clinician having to seek out the specific knowledge.

The IOM Report finds that currently, knowledge about best care is not applied systematically of expeditiously to clinical practice, and that there are insufficient tools and incentives in place today for promoting rapid adoption of best practices. Far more sophisticated clinical decision support systems (CDSS) must be in place to assist clinicians and patients in selecting the best treatment options and delivering safe and effective care.

Practice Guidelines (Evidence-Based)

Clinical practice guidelines may be defined as systematically developed statements to assist practitioner and patient to make decisions about appropriate health care for specific clinical circumstances. Institute of Medicine, 1992. Guidelines build on synthesis of the evidence, but go one step further to provide formal conclusions or recommendations about appropriate and necessary care for specific types of patients. Lohr, et al., 1998. Guidelines have proliferated at a rapid pace throughout the last decade or so. The Agency For Health Care Research and Quality led to the specification of about 20 guidelines, which led to the establishment of the Evidence-Based Practice Centers in partnership with private sector organizations (Lohr, et al., 1998). Guidelines may vary in degree, so judgment must be exercised in this process because the evidence base is sometimes weak or conflicting, or lacking in the specificity needed to develop recommendations useful for making decisions about individual patients in particular settings (Lohr, et al., 1996).

Clinical practice guidelines are developed through a rigorous methodological approach requiring review and consideration of the available medical literature. Practice guidelines define the role of specific diagnostic and therapeutic modalities, including non-invasive and invasive procedures, diagnosis and management of patients with various cardiovascular diseases. The guidelines are evidence-based, and assist clinicians in their clinical decision making processes by describing a range of generally acceptable approaches for the diagnosis, management or prevention of specific diseases or symptoms. Practice guidelines attempt to define practices that meet the needs of most patients in most circumstances by categorizing recommendations within a classification system. American College of Cardiology Foundation.

Computer-Based Clinical Decision Support Systems

A clinical decision support system (CDSS) combines clinical expertise with available best evidence to realize the best care to be provided to a patient. A CDSS is defined as software that integrates information on the characteristics of individual patients with a computerized knowledge base for the purpose of generating patient-specific assessment or reconsideration. CDSSs are designed to help patients and clinicians make clinical decisions about, for example, preventive and monitoring tasks, prescription of drugs, diagnosis, etc. A CDSS for computer-associated diagnosis and management aids (CADMA) requires 1) an expansive knowledge base covering the full range of diseases and conditions, 2) detailed patient-specific clinical information, and 3) a powerful computational engine that employs some form of probabilistic decision analysis. Many professional societies (ACP-ASIM, ACR, Ace, . . . ) prepare the guidelines or knowledge base used to implement evidence-based care of patients (paper and electronic form). The clinician selects the clinical practice guideline which fits the current patient's statistics, or what knowledge is relevant to the current care criteria. FIG. 1 is an example of a guideline for detecting and qualifying thrombosis.

The use of a CDSS for prevention and monitoring purposes has been shown to improve compliance with guidelines in many clinical areas, and computerized prescription of drugs offers great potential benefit in such areas as dosing calculations and scheduling, drug selection, screening for interactions, and monitoring and documentation of adverse side effects is far more limited because such applications generally the linkage of more comprehensive patient-specific clinical information with the medical knowledge base. CDSS diagnostic systems (executable clinical practice guidelines) require detailed, patient specific clinical information (history, physical results, medications, laboratory test results, etc.) to be integrated with clinical workflow. The executable guidelines make knowledge readily available to the clinician, without the clinician having to seek out the specific knowledge.

Using conventional systems, a clinician may access and execute the guideline by starting at a first step of the guideline, and proceeding in accordance with the patient's treatment. But at times clinicians want to explore possible outcomes (as defined by the practice guidelines). To that end, commonly-owned U.S. Provisional patent application No. 60/591,071, filed Jul. 26, 2004, is directed to the problem of providing a clinician with the ability to simulate procession through a series of steps of a selected guideline, or portion thereof, for determining possible outcomes associated with following the series of steps of the guideline (the content of which is incorporated herein by reference). And while it is desirable to for a CDSS to be able to simulate process of a practice guideline, it is also desirable for a clinician to have an ability to view the content of the guideline in the correct level of extraction to meet his immediate needs. That is, it is desirable to be able to navigate a practice guideline such that he/she has an ability to read, navigate, search and determine the relevant clinical guidance at the correct level of abstraction relevant to the current clinical context.

To that end, the present invention is directed to the development of a computing system and method for providing an investigator utilizing a technological (e.g., engineering) application, where the application is in a form of a technical guideline and or knowledge base, with an ability to change the technical guideline/knowledge base, and change the level of abstraction in the guideline. The user may manually choose a guideline and level of abstraction, or the DSS as disclosed herein may automatically choose a guideline and level of abstraction therein based on control signal generated in consideration of the user context, which may be defined by an imported data file, etc., as would be known to those skilled in the art.

In one form, the invention is directed to a clinical decision support system, for medical related applications. The inventive CDSS would include an ability to access a set of guidelines, i.e., medical care guidelines and/or knowledge base, which may be automatically chosen by the context of care, and the level of abstraction of the automatically determined guideline, again based on the context of care. The context of care may be communicated to the CDSS by various means, such as a control signal or electronic file including context information for the particularly required treatment. The CDSS may also operate in manual mode, where a clinician is provided with an ability to effectively handle and extract information which is most valuable in view of user-input context, or choice of a guideline for a critical pathway, and readily (and conveniently) make any information in the guideline and/or knowledge base, at any degree of abstraction of the guideline as desired by the clinician from the mass of information available.

That is, the present inventions include a CDSS and method, which enables navigation over different levels of abstraction of various clinical practice guidelines for a particular context of care. Such a CDSS and method aids the user by providing an indicator (visual or otherwise known to those skilled in the art) on the current step in the guideline, during the current context of care, and to increase/decrease the level of detail provided by the system.

In the broader sense, the present invention may be implemented to ease the use of, and facilitate access to available scientific information comprising any practice guideline. One skilled in the art will understand the value of being able to access the desired level of abstraction in the guideline or knowledge base through implementation of the visual navigator contracted into a user interface for control of abstraction once in a guideline/knowledge base Whether through implementation of CDSS for healthcare applications, or more broadly with the use of computer driven technical guidelines/knowledge bases, including a UI which allows user interaction with the guideline/knowledge base, the user may adjust the level of abstraction according to the context of the problem (e.g., care), using the inventive concepts disclosed herein, whether operating in automatic or manual mode. More particularly, the present invention may be operated in two modes. The first mode is automatic, where a technical or clinical application submits a description of the technical/clinical context, and the inventive DSS/CDSS server selects the proper guideline.

The DSS/CDSS may also provide a pointer or visual navigator in the UI to indicate the current level of abstraction in the guideline (or the relevant knowledge in the guideline). The clinician may then change the level of abstraction using the visual navigator. The second mode of operation is manual. During manual operation, the DSS/CDSS provides that the user/clinician simply click on a guideline, and thereafter a section of the guideline to communicate to the DSS/CDSS the context of information needed. And as mentioned in the automatic context, the user interface provides the visual navigator (pointer), which allows the user to increase or decrease the level of granularity, which is presented. For example, FIG. 2 shows that the user, by clicking on the AHCPR Unstable Angina guideline step, will be presented with the details of that guideline, and clicking the less detail button returns the user to the guideline currently shown in FIG. 2.

Figure 1:
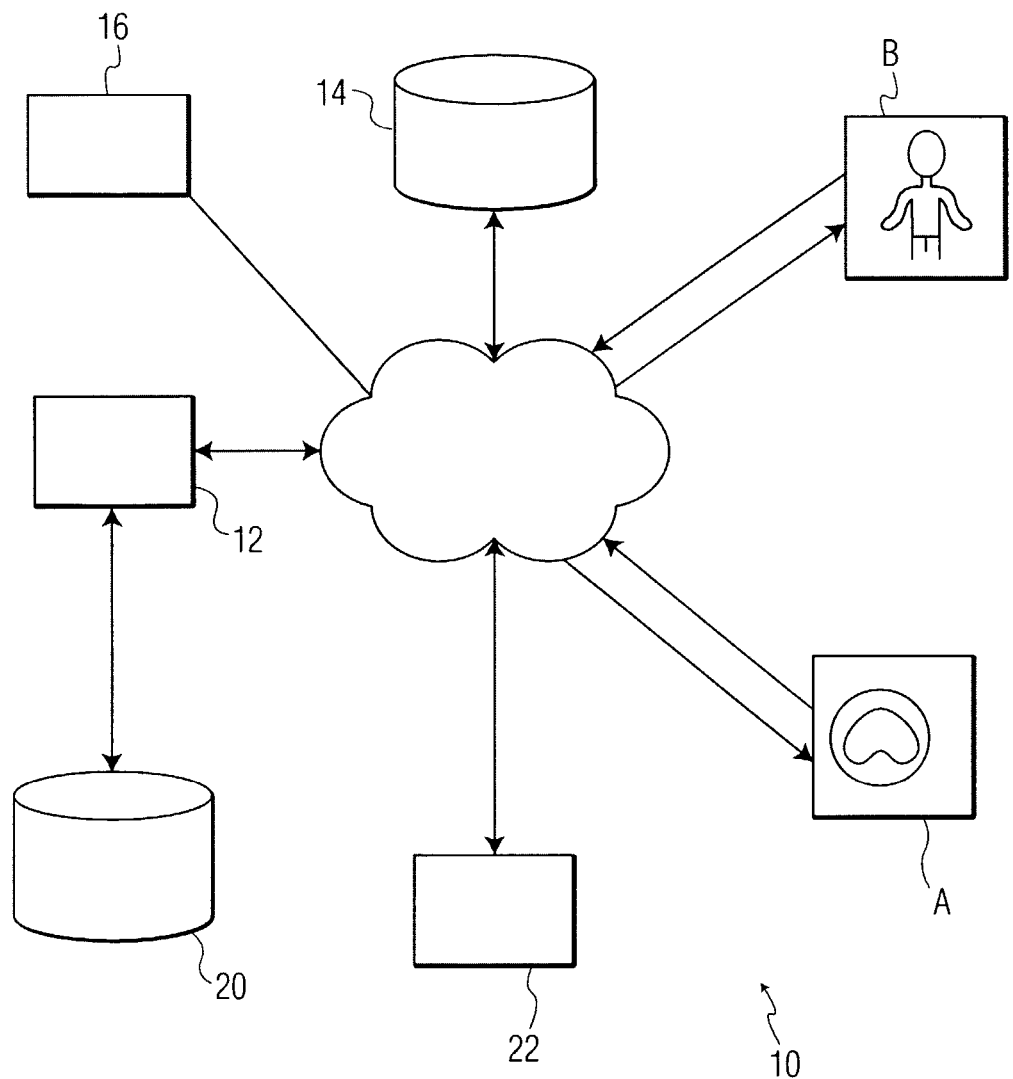
FIG. 1 shows an exemplary CDSS 10 for use in assisting in providing healthcare to a patient in accordance with the present invention.

The inventions disclosed herein include, but are not limited to, clinical decision support systems (CDSSs) with a user interface for the visualization and navigation of a medical clinical practice guideline, connection to data sources, and a visual navigator to the user on the current step in a guideline, or the relevant knowledge in the guideline to access the clinical information available at the appropriate level of abstraction in accord with the context of care for a particular situation. The reader should note, however, that the description of the invention with respect to the use of medical clinical practice guidelines is merely on implementation of a decision support system, more broadly, which may choose, allow access to a guideline from a database of guidelines, and using a user interface, change the level abstraction of the information/direction offered by the guidelines/knowledge base.

Broadly, the use of practice guidelines facilitate evidence-based practice. Evidence-based practice is the integration of best research evidence with clinical expertise and patient values. Best research evidence refers to clinically relevant research, for example, patient-centered clinical research into the accuracy and precision of diagnostic tests, the power of predictive markers, the efficacy and safety of therapeutic rehabilitation and preventative regimens. The best care results from the conscientious, explicit and judicious use of current best evidence and knowledge of patient values by well-trained experienced clinicians. The DSS or CDSS of this invention makes available, and navigable by level of abstraction, access to the "current" best evidence and knowledge (in the context of the context, e.g., patient, values).

The term database as used herein refers to a structured storage, but is not limited thereto, and may further refer to a data source that is not structured, such as a repository. The CDSS 10 is implemented using at least one processor and at least one storage medium accessible by the at least one processor. Components of the CDSS 10 include the instructions which define the operation of the CDSS, loaded down on CDSS server 12; at least one patient database 14 for storing patient data including information relating to the patient and/or his treatment (such as for storing personal data relating to a plurality of patients) and a lab data database 16 (such as for storing results of lab tests performed on a plurality of patients); a guideline database 20 or repository 20; and a system user interface 22. The couplings between the components of the CDSS 10 may be wired or wireless, and may be provided by one or more networks, such as a LAN, a WAN, an intranet, the Internet or a combination thereof.

The respective components of the CDSS 10 may share resources of the at least one processor and the at least one storage medium, or may have exclusive use of one or more of the resources. The at least one processor may include, for example, a personal computer, a microprocessor, a handheld computing device, a server, etc. The at least one storage medium may include, for example, a hard drive, a CD-ROM, RAM, flash memory, volatile memory, non-volatile memory, etc.

The CDSS server 12 may reside on a server and/or storage accessible thereby for execution by the server, where the server is accessible by a plurality of computers. For example, a user, such as a clinician, may operate a workstation, such as a personal computer, in order to use the server 12, where execution of the server 12 is performed at the server or at the workstation. Alternatively, the CDSS system software (as server) may reside on one or more workstations and/or storage devices accessible thereby for execution by the workstation. Furthermore, the CDSS server 12 may be embedded within or linked to another system, such as an administrative information system (e.g., for a hospital, nursing home, laboratory, etc.). Exemplary applications for the CDSS include assistance in resource management and/or planning and/or quality assurance.

The CDSS server 12 may access a selected guideline from the guideline database 20, where the clinical practice guideline is selected for appropriately guiding the user in the patient's current treatment. The guideline may be selected by the user by instructing the CDSS server 12 to access the selected guideline, or automatically by the server 12 in accordance with clinical context related data available to the CDSS server 12. Examples of context include the patient's present state, medical history, care provided so far, etc. A clinical application having the necessary interfaces may be used to submit patient data, including clinical context data, to the server 12. Alternatively, the system user interface 22 may be used to allow the user to enter patient data. A copy of the selected guideline or links thereto may be stored temporarily or permanently, such as at the user's work station, with the patient's data in the patient database 14, and/or in a workspace provided by and/or accessible by the guideline database 20 or the CDSS server 12. The stored copy may be customized for the individual, such as by eliminating or bypassing certain steps of the guideline. For example, a clinician may use a guideline-editing tool to create a personalized version of the guideline.

The guidelines stored in the guideline database 20 are preferably evidence-based, and developed in accordance with experience and research of experts in the field. The guidelines are encoded by appropriate encodings, such as ASBRU, GLIF, EON, GUIDE, PRODIGY and PROforma, etc. The guideline database 20 is preferably searchable for finding and selecting a particular guideline or the guideline that best meets criteria for guidance in the patient's current treatment, or for simulation of treatment of the patient. The guideline is typically selected to provide clinical guidance for treatment within a context best matching a combination of at least one of a patient context, user context, care context, etc.

Interaction between the CDSS server 12 and the user is provided via the system user interface 22. The system user interface 22 preferably includes a guideline interface, which presents a representation of the guideline being executed to the user. The guideline user interface may include a display, such as for a handheld or desktop computing device, a pointing device and/or a keyboard, etc. The guideline user interface may include a graphical user interface (GUI), but need not be graphical. For example, a telephone voice activated system that uses voice recognition technology may be used, and/or menu choices and/or prompts may be audio messages. User responses may be provided by key pushes and/or voice responses.

Figure 2:
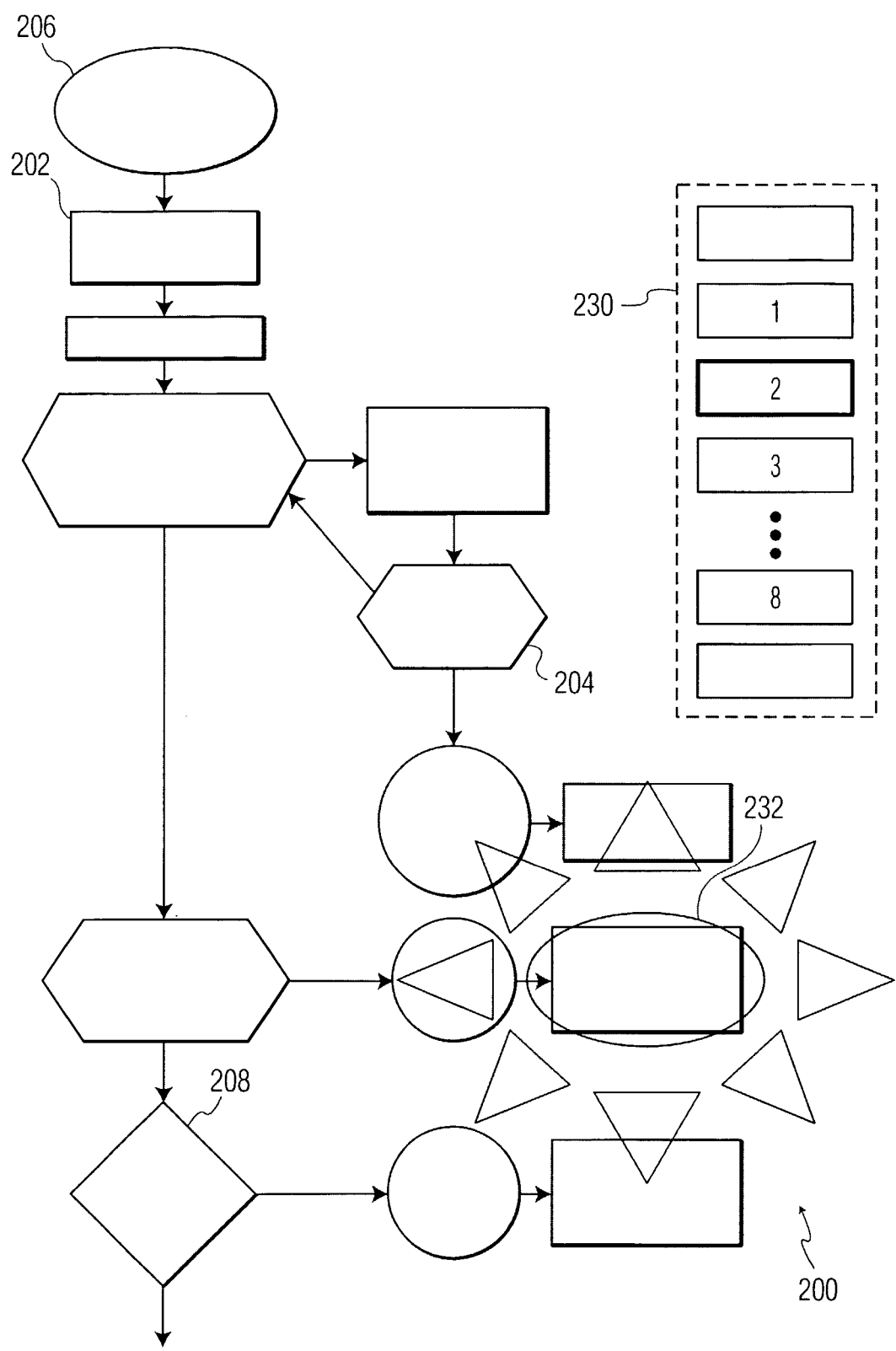
FIG. 2 shows a detailed view of a display of the present invention, which includes a clinical practice guideline and a visual navigator for changing abstraction levels of the guideline.

An exemplary GUI for an exemplary clinical practice guideline 200 is shown in FIG. 2. The individual steps of the guideline 200 include a variety of types of steps, including an action step exemplified by step 202, instructing a clinician or a component of a system such as CDSS 10 shown in FIG. 1 that an action is taken (such as, gathering information, performing tests, providing treatment, or jumping to another step of the guideline or of a different guideline); a choice step exemplified by step 204 for prompting a user to decide the next step to perform from at least two steps; a patient state step exemplified by step 206 representing the current state of the patient or a patient related condition; and a case step exemplified by step 208, at which at least one algorithm is performed for deciding which step to perform next.

The GUI shown represents the guideline 200 as a flowchart. The GUI may represent the guideline in other formats, for example as a text document. An indicator 232 is displayed to show the current step being processed during execution of the guideline. A visual navigator 230 is displayed to show the selected level of detail or abstraction according to the context of care. The user may adjust the level of granularity of the guideline using the visual navigator as included in the UI 22.

That is, the UI allows the user to increase or decrease the level of granularity that a guideline is presented to the user. For example, and as shown in FIG. 2, a user's click on the AHCPR unstable angina guideline presents the user with the details of that guideline. Clicking the lest detail button of the visual navigator returns the user to the guidelines as presently presented (FIG. 2).

With respect to FIG. 1, A and B situations, the CDSS server 12 may automatically make selections and determines the relevant information/parts of a guideline by establishing context. In automatic operating mode, the CDSS receives data defining the context for the clinical situation by any clinical application known to those skilled in the art. For example, the context could be described as follows:

```
Context {
    Patient Context {
        Patient Age;
        Patient Gender;
        Associated Condition: Coded concepts that indicate
        conditions;
    }
    User Context {
        User Role: physician, nurse, medical student ...;
    }
    Care Setting Context {
        Setting: ICU, Ambulatory care, ...;
        Modality: CT, X-ray, Clinical Information System, ...;
    }
```

-continued

```
Other contexts {
    Date, Time;
    /* some guidelines use different sub-guidelines
    (weekdays/weekends/day/night)*/
    }
}
```

The proper level of abstraction of the guideline is determined by the current context automatically, and indicates the level of abstraction via the visual navigator included in the UI. To provide seamless transitions among different levels of abstraction requires that additional meta-data be added to guideline encoding models such as the GLIF & GEM models. A solution could be a two-way W3C Xlink type of URL. Such a solution, however, should be readily known to those skilled in the art. In manual mode, a user selects a guideline through the UI, and uses the visual navigator to find the proper level of information available.

Figure 3:
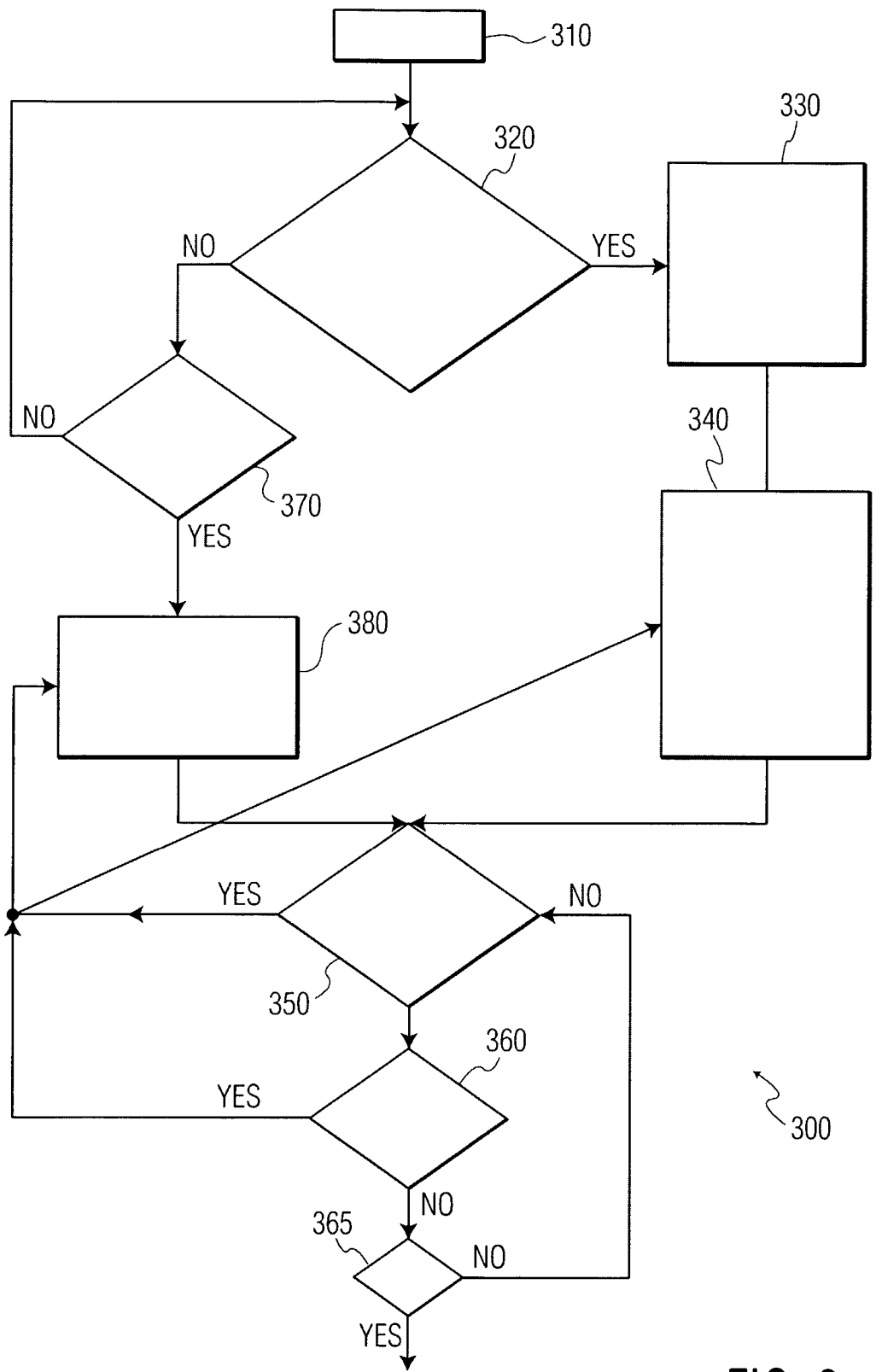
FIG. 3 is a flow chart showing operation of a method of implementing the present invention.

A flowchart 300 is shown in FIG. 3, illustrating the steps of an embodiment of a method of this invention. Block 310 indicates the initiation of the CDSS as the first step of the method. Block 320 indicates a decision the CDSS has to make as to whether it is in automatic mode, or manual mode. The receipt by the CDSS of an electronic file defining the context of care puts the system into automatic mode. And if in automatic mode, the step, which is highlighted in block 330, is implemented by the CDSS. That is, the CDSS receives a file or control signal that defines the clinical context of care of which the clinician needs to investigate. The CDSS uses the electronic information or control signal or signals to choose the appropriate guideline in the next step of the method, as shown in box 340 of FIG. 3. The guideline and at least the visual navigator in the UI are displayed.

The next step in the method, highlighted as block 350, offers the user the choice of changing the level of abstraction of the guideline, in automatic mode. Block 360 shows a step wherein the CDSS "looks" for a user input (in some electronic, computer understandable form) from the UI seeking to change the level of abstraction. Block 365 shows the step which ends the process. If there is no automatically generated and received electronic file or electronic control signal, which would compel operation in automatic mode, the CDSS waits for a user to choose (click on) a guideline, the step highlighted by block 370. The CDSS then displays the guideline, including the visual navigator defining the present level of abstraction (block 380). The algorithm then moves on waiting for a user to change the level of abstraction, via the user interface, in the step of block 350. The CDSS then "looks" for an indication that the user desires to manually change guidelines in the step of 360.

The reader should note that any embodiment shown herein is for explanatory reasons only, and is not meant to limit the scope, which scope should only be limited by the claims appended hereto. That is, the described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

The invention claimed is:

1. A computing system for executing an executable practice or professional guideline to receive practice or professional information or knowledge contained in the guideline at a proper level of abstraction to meet a context definition appropriate for a slated use of the practice or professional information or knowledge, the computing system comprising:
  a guideline repository which stores a plurality of the executable practice or professional guidelines and from which selected practice or professional guidelines are retrievable;
  at least one interface providing for entry of one of context data and a control signal defining a context of the practice or professional information or knowledge;
  a display;
  at least one server which receives said context data or control signal, automatically chooses one of the executable practice or professional guidelines stored in the guideline repository in accordance with the received context data, and causes the display to display the chosen guideline and to display a visual navigator, the visual navigator including a list identifying each of a plurality of available levels of guideline abstraction and an indicator which indicates with which of the available levels in the list the chosen guideline is displayed; and
  a user input device by which a user changes the displayed guideline resulting in a new guideline being displayed at a new level of abstraction and the visual navigator displaying the new level of abstraction, such that the level of abstraction is changeable by the user input in both a manual mode and an automatic mode.

2. The computing system as set forth in claim 1, wherein the practice or professional guideline includes a clinical practice guideline developed based on medical literature and defining a role of specific diagnostic and therapeutic modalities, including non-invasive and invasive procedures, diagnosis, and management of patients with various diseases, the clinical practice guidelines describing a range of generally acceptable approaches for diagnosis, management, and prevention of specific diseases or symptoms.

3. The computing system as set forth in claim 2, further comprising:
  at least one data source which provides patient data, selected patient data being retrieved from the at least one data source during execution of the retrieved guideline.

4. The computing system a set forth in claim 3, wherein the at least one server:
  determines if the selected patient data to be retrieved from the at least one data source are available;
  provides a notification upon an availability of new patient data via the at least one data source; and
  when the new data are usable for the selected patient data that was determined to be not available, provides for processing the new patient data including providing for using the new patient data for providing the selected patient data that was not available for use in executing the displayed guideline.

5. A non-transitory computer readable medium carrying a program which when executed controls a processor to perform the steps of:
  selecting a clinical practice guideline developed based on medical literature and defining a role of specific diagnostic and therapeutic modalities, including non-invasive and invasive procedures, diagnosis, and management of patients with various diseases, the clinical practice guidelines describing a range of generally acceptable approaches for diagnosis, management, and prevention of specific diseases or symptoms, the selected clinical practice guidelines being selected from among a plurality of clinical practice guidelines stored in a database in response to receipt of at least one of (1) data defining a context of a task at hand and a user's manual selection via a user interface (UI);
  controlling a display to display the selected clinical practice guideline for user review, a visual navigator which includes a list of available levels of abstraction of the selected clinical practice guideline, and an indication of which of the available levels of abstraction is being displayed; and
  in response to a user input, selecting a different level of abstraction from the list of available levels of abstraction via the user interface to change a current level of abstraction of the displayed clinical practice guideline.

6. The computer readable medium as set forth in claim 5, wherein the data defining the context of the task at hand is medical, the context concerns a medical patient, and the guidelines are clinical practice guidelines.

7. The computer readable medium as set forth in claim 5, wherein the context is provided automatically to select the practice guideline.

8. The computer readable medium as set forth in claim 5, further including:
  interacting with the list of available levels of abstraction of the displayed navigator to change from the current level of abstraction to a different level of abstraction.

9. A computer based clinical decision support system comprising:
  a database which stores a plurality of medical related clinical practice guidelines having a plurality of levels of abstraction;
  a display device;
  a user input device through which a user inputs instructions to change the level of abstraction; and
  at least one processor which is programmed to:
    retrieve a selected medical related clinical practice guideline from the database, and
    control the display device to display the selected medical related clinical practice guideline and a navigator which indicates a current level of abstraction of the displayed selected medical related clinical practice guideline.

10. The system as set forth in claim 9, wherein the processor is further programmed to:
  in response to receiving new medical data, selecting a new medical related clinical practice guideline and a new level of abstraction and a new level of abstraction;
  displaying the new medical related clinical practice guideline and an indication of which of the available levels of abstraction the new medical related clinical practice guideline is being displayed.

11. The system as set forth in claim 9, wherein the processor is further programmed to:
  receive medical data and control signals;
  retrieve one of the plurality of medical related clinical practice guidelines and one of the levels of abstraction automatically based on the received medical data and control signals; and
  display the retrieved one of the medical related clinical practice guidelines and an identifier of the retrieval level of abstraction.

12. The system as set forth in claim 9, wherein the displayed navigator includes a list identifying each of a plurality of available levels of guideline abstraction of the displayed clinical practice guidelines and an indicator which indicates in which of the available guideline abstraction levels in the list the chosen guideline is displayed.

13. The system as set forth in claim 12, wherein the user input device is configured to select one of the available levels of abstraction from the level of abstraction list and the processor responds to the selection of the selected level of abstraction by causing the display to display one of the clinical practice guidelines at the selected different level of abstraction and indexes the visual navigator to indicate the new displayed level of abstraction.

14. The system as set forth in claim 9, wherein the clinical practice guidelines are developed based on medical literature and define a role of specific diagnostic and therapeutic modalities, the clinical practice guidelines describing a range of generally acceptable approaches for diagnosis, management, and prevention of specific diseases or symptoms.

15. The system as set forth in claim 14, wherein the user input device selects one of the available levels for abstraction in the displayed list of available levels of abstraction to input the instructions to the processor to change the level of abstraction.

16. A method for automatically accessing a proper medical related clinical practice guideline for available patent data and a proper level of abstraction of the guideline based on the available patient data including the steps of:
   in response to receipt of the available patient data, selecting with a processor a first medical related clinical practice guideline and a first level of abstraction from a guideline memory that stores a plurality of medical related clinical practice guidelines;
   displaying the selected first medical related clinical practice guideline, an identifier of the selected first level of abstraction of the selected first medical related clinical practice guideline and a list of available levels of abstraction of the selected first medical related clinical practice guideline for user review;
   in response to a user input through a user interface, selecting a second medical related clinical procedure guideline and a second level of abstraction; and
   displaying the second medical related clinical practice guideline, the identifier of the second level of abstraction of the second medical related clinical practice guideline and a list of available levels of abstraction of the second medical related clinical practice guideline.

17. The method as set forth in claim 16, wherein the selecting step includes:
   selecting one of the available levels of abstraction from the list of available levels of abstraction with the user interface.

18. The method as set forth in claim 16, further including:
   in response to additional patent data become available, automatically with the processor, selecting a third medical related clinical practice guideline and a third level of abstraction; and
   displaying the third medical related clinical practice guideline, the identifier of the third level of abstraction, and the list of available levels of abstraction.

19. The method as set forth in claim 16, wherein the list identifies each available level of abstraction and the selected level identifier marks one of the identifiers in the list.

20. The method as set forth in claim 16, wherein the clinical practice guidelines describe a range of generally acceptable approaches for diagnosis, management, and prevention of specific diseases or symptoms including a role of specific diagnostic and therapeutic modalities, including non-invasive and invasive procedures, diagnosis, and management of patients with the specific diseases or symptoms.

\* \* \* \* \*